United States Patent [19]

Wolfram et al.

[11] Patent Number: 4,968,497

[45] Date of Patent: Nov. 6, 1990

[54] SKIN TANNING COMPOSITION AND METHOD

[75] Inventors: Leszek Wolfram, Stamford, Conn.; Alexander C. Chan, Mineola; Thomas M. Schultz, Highland Mills, both of N.Y.; Bryan P. Murphy, Monroe, Conn.

[73] Assignee: Clairol Incorporated, New York, N.Y.

[21] Appl. No.: 237,123

[22] Filed: Aug. 26, 1988

[51] Int. Cl.$^5$ .................... A61K 7/021; A61K 7/40; A61K 7/42

[52] U.S. Cl. ............................. 424/59; 8/408; 424/63; 424/78; 424/80; 424/81; 514/937

[58] Field of Search ................... 424/59, 63; 8/408

[56] References Cited

U.S. PATENT DOCUMENTS

| | | | |
|---|---|---|---|
| 3,698,852 | 10/1972 | Pantzer et al. | 8/408 |
| 4,453,941 | 6/1984 | Jacobs | 424/59 |
| 4,507,277 | 3/1985 | Cao et al. | 424/59 |
| 4,515,773 | 5/1985 | Herlihy | 514/785 |
| 4,522,808 | 6/1985 | Jacquet et al. | 424/59 |
| 4,609,544 | 9/1986 | Herlihy | 424/60 |
| 4,776,857 | 10/1988 | Carroll et al. | 424/59 |
| 4,786,493 | 11/1988 | Smith et al. | 424/59 |
| 4,806,360 | 2/1989 | Leong et al. | 424/59 |
| 4,844,884 | 7/1989 | Tur | 424/59 |

FOREIGN PATENT DOCUMENTS 69780  3/1987  Australia .............................. 424/63

OTHER PUBLICATIONS

Sagarin Cosmetics Science & Technology, 1957, pp. 189–196.

Primary Examiner—Dale R. Ore
Attorney, Agent, or Firm—Sandra M. Nolan

[57] ABSTRACT

The present invention relates to a method of imparting a controlled tanning of skin by treating the skin with an aqueous medium containing melanin or a precursor of melanin.

27 Claims, No Drawings

SKIN TANNING COMPOSITION AND METHOD

The present invention relates to a novel composition and method for tanning human skin.

BACKGROUND OF THE INVENTION

The structure of skin can be visualized best in terms of its basic division into two anatomically distinct layers: the epidermis and the dermis. The epidermis is the only portion of the skin normally visible. It is a multicellular layer and gives rise to all the glands and appendages of the skin. The dermis forms the bulk of the living skin and fundamentally has a fibrous structure.

The epidermis is composed of two principal layers: the stratum malphighii (the wet living epidermis) and the stratum corneum or horny layer (the dried, keratinized, "dead" outermost layer). The epidermis contains two distinct cell types: keratinocytes which are the primary structural cells comprising 90-95% of the epidermis and melanocytes which are the melanin synthesizing cells, comprising 5-10% of the cells normally found in the basal layer of the malphighian zone.

The color of human skin is due to presence of melanin pigment within the skin, which pigment is usually in the form of discrete granules called melanosomes. The latter are generated in the viable layer of epidermis by pigment cells (melanocytes). The skin color is genetically controlled and people of different races exhibit characteristic features of pigmentation both in their intensity and chromatic tone. The depth of color in human skin is a function of the quantity of the melanin pigment present, its chemical characteristics and distribution. The presence of melanin in the skin provides a marked photoprotective role, i.e., it acts as an oxygen radical scavenger and as a sunscreen. Black and darkly pigmented people are far less susceptible to chronic actinic damage from ultraviolet light than are fair skin individuals.

It is well known that individuals can augment their skin color by tanning. Exposure to ultraviolet radiation, whether from sunlight or artificial sources such as sunlamps, results in formation of additional pigment in skin. The tanned skin is almost universally regarded as a positive aesthetic attribute, and it is highly desired as a sign of beauty and health. A high proportion of fair-skinned (Caucasian) individuals have this desire.

Unfortunately, this desire for tanning subjects skin to the damaging effects of ultraviolet radiation. The most readily perceived and acutely felt effects of ultraviolet exposure is the erythema (skin reddening and burning) but this is only a prelude to actinic elastosis (sailor's skin) and possibly even squamous cell carcinoma.

Ultraviolet light that reaches the earth's surface is divided generally into a higher energy region (UVB) having a wavelength band of 2900 to 3400 Angstroms, and a lower energy region (UVA) having a wavelength band of 3400 to 4000 Angstroms. Radiation in the UVB range usually causes the skin to burn as well as tan. A satisfactory level of tanning and somewhat less burning can be attained by prolonged exposure to ultraviolet light in the UVA range.

Some protection against sunburn and other ultraviolet radiation exposure related problems is provided by sunscreens, i.e., materials which are effective in absorbing ultraviolet radiation in the range of 290-320 nm. While application of these may prevent skin burn, it also retards or inhibits tanning. Here, indeed, lies the dilemma of tanning. The melanin pigment itself is one of the best protecting agents against the harmful effects of ultraviolet radiation but to generate it by tanning, one pays the price of sun-induced skin damage.

To satisfy the aesthetic longing for tan skin without the necessity of exposing oneself to the harmful effect of prolonged sun exposure, a number of types of skin coloring products have been developed, two of which are on the market.

The first type of products consists of skin gels and lotions which contain dyes and/or pigments that when spread on skin surface mimic the tanning effect. However, while the color characteristics (natural look, tone, etc.) obtained with these products are satisfactory, the surface deposits are only of temporary nature, they stain clothing and undergo ready rub-off.

The second type of products, of a more durable character, are those that are based on materials that interact with skin such as iodine, potassium permanganate and dihydroxyacetone. Of these, only the dihydroxyacetone has gained some limited commercial importance, but even in this case, the color effects obtained are not aesthetically satisfying.

In addition, a type of product based on the use of a melanin precursor in combination with an enzyme catalyst and frequently an activator have also been described in the literature. U.S. Pat. No. 4,609,544 discloses tanning by applying a composition comprising a melanin like dye, a peroxidase enzyme and hydrogen peroxide in a cosmetic base suitable for topical application to the skin. U.S Pat. No. 4,515,773 discloses a skin tanning composition containing a melanin precursor and a tyrosinase enzyme in a cosmetic base.

However, these prior art compositions require the use of enzymes and oxidative agents in combination with the melanin precursors and appear to deposit the melanin-like materials only on the exterior of the skin. As the melanin molecule is incapable of penetrating the skin, only superficial external tanning results, which is readily removed by rinsing with water or rubbing with a towel. There is truly no commercially available product that will mimic skin tan with respect to its durability, aesthetics of color and photo-protection. A need thus clearly exists for a preparation to produce a durable and natural appearance of tan combined with protection against potentially harmful sun radiation.

Accordingly, it is an object of this invention to provide an improved sunscreen capable of reducing burning and promoting tanning.

BRIEF DESCRIPTION OF THE INVENTION

It has now been unexpectedly found that superior skin tanning and solar radiation protection can be provided to human skin by the application of a composition containing a tanning agent which is a melanin precursor or a melanin precursor like material, the composition being substantially free of added enzyme and peroxide.

Melanin, which is the pigment formed in the skin upon tanning, is known to be an excellent sunscreen. The application of the melanin precursors of the present invention to the skin surface not only provides a desirable, controlled tan color to the skin, but also provides a measure of protection against harmful actinic rays. Therefore, the present invention provides an improved means for both tanning and photoprotection.

The substantial amount of evidence that points to the photoprotective role of the melanin led applicants to conclude that the melanin generation process of the present invention not only results in a desirable tan but may also provide a useful means of protection against actinic radiation.

DETAILED DESCRIPTION OF THE INVENTION

Unless stated otherwise, all percentages recited herein are weight percentages based on total composition weight.

It appears that the melanin formation resulting from the use of the melanin precursors of the present invention takes place in the stratum corneum. Therefore, the tanning produced by the present invention, while not as durable as naturally occurring tanning resulting from melanin pigmentation in the malphigian layer, is substantially more durable than tanning pigmentation caused by prior art methods wherein the melanin formation takes place on the surface of the skin. Notwithstanding the difference in the location of natural melanin pigmentation and that produced by the present invention, the aesthetic effect resulting from pigmentation provided by the present invention is very similar to tanning and can also provide a high degree of protection against solar radiation.

The desired formation of melanin pigment and resulting tanning effect can be readily accomplished by treatment of skin with one or more appropriate tanning agent(s), which are melanin precursors or melanin precursor-like materials. While the term "tanning agents" and "agents" are used in the specification to describe these precursors and precursor like materials, it should be noted that these substances may be termed "catalysts" or "assistants" as well.

Suitable melanin precursors and precursor-like materials are synthetic compounds which are capable of forming melanin and mellanin-like compounds. Typically, they include compounds such as 5,6-dimethoxyindole, 5,6-methylenedioxyindole, 3,4-dihydroxyphenylalanine and its derivatives, particularly cysteinyl DOPAs like 2-cysteinyl-DOPA and 2,5-dicysteinyl-DOPA 5-cysteinyl-DOPA; dopamine, 5,6-dihydroxyindole and its derivatives, particularly N-alkyl-5,6-dihydroxyindole wherein the alkyl group contains from 1 to 6 carbon atoms, and 5,6-dihydroxyindole-2-carboxylic acid and the like. Mixtures are operable.

Two additional aspects of the present invention deserve noting. Firstly, the pigment formation does not require contribution from either exogenously applied or indigenously present enzymes (such as tyrosinase or peroxidase) which are known to catalyze the conversion of melanin precursors to melanin. Secondly, conventional tanning effects are generally associated with a delay, i.e., a time interval ranging from 18 hours to several days between sun exposure and melanin formation. Surprisingly, with the present invention the melanin generation begins from the first moment of contact of the melanin precursor with the skin. Although exposure to sunlight is not necessary, pigment formation is accelerated by subsequent exposure to sunlight. Both of these phenomena, surprising as they are, are of clear benefit to the individual seeking tanning.

Notwithstanding the obvious difference in the mechanism of pigment formation that takes, place when practicing the present invention and the mechanism controlling conventional tanning, and irrespective of the difference in the location of the indigenous melanin and that produced by the present invention, the appearance of tan in both instances is very similar, as is the afforded photoprotection.

The time required for the darkening or tanning of the skin following the application of a composition based on the present invention depends on the type of precursor used, individual skin characteristics and whether skin is exposed to sunlight. Exposure to sunlight may significantly accelerate the tanning effect.

The effects associated with sunlight or ultraviolet exposure, which generate the melanin pigment in the stratum corneum, are quite different from those which take place in the course of conventional tanning. In the latter case, the appearance of tan is generally delayed by 1-3 days after sun ultraviolet exposure and is usually preceded by an erythemal stage (skin reddening or burn) resulting from the skin injury attendant upon prolonged sun exposure. With the present invention, the tan is rapidly generated in approximately 2-30 minutes, with no evidence of, or need for, an erythemal stage.

Usually, the tanning agents of the present invention will be applied to skin in a suitable topical cosmetic base in the forms of aqueous lotions or gels. Typically, these agents will be present in a concentration range of 0.1 to 10% by weight, based on the total weight of the composition. As used hereinafter, all references to % by weight will refer to % by weight of the total composition. A combination of precursors may be used to modulate the intensity and color tonality of the desired tan.

Lotions or gels can be prepared by methods well known in the art. For example, a tanning lotion can be prepared by dissolving the required quantity of one or more agents in 40% aqueous ethanol containing 5% by volume of glycerin. Aqueous or alcoholic gels based on Carbopol (polymers of acrylic and methacrylic acids), hydroxyethylcellulose, guar, and the like, in suitable amounts, can serve as an appropriate base or carrier for the melanin precursors or other agent. The compositions may also contain suitable quantities of emollients, perfumes, etc.

If desired, known sunscreening agents can be compounded with the tanning agents without affecting the activity of the latter to generate the melanin pigment.

The presence in the stratum corneum of certain metal salts can have an accelerating effect on the formation of melanin as described herein, even in the absence of exposure to actinic energy of sunlight. Acceleration of melanin formation can be increased by as much as 5 to 10 times the normal rate, depending upon the particular metallic salt being employed and the melanin precursor involved. Among the metallic cations particularly useful for this purpose are those of copper, iron, zinc and manganese. As these metallic cations have high affinities for the proteins of the stratum corneum they can be readily introduced into the skin tissue by simple treatment of skin with compositions containing such cations. These compositions may vary from lotions and rinses to mousses and shampoos to sprays and soaps. The concentration of metal cations will be determined by the nature of the formulation employed but, in most cases, will be generally in the range of about 0.01 to about 2%.

According to a first embodiment of the process of the present invention, an aqueous solution or dispersion of a tanning agent is applied to the skin such as by swabbing or the like, very much in the manner in which most skin products are used. The concentration of the agent that is employed depends on the level of the depth of the desired tanning effect. Generally, concentrations of melanin precursor or other agent of between about 0.1 and about 10% by weight will produce a desirable tanning effect. Between about 0.1 and about 1.0, and preferably about 0.2 to about 0.8 percent, of the tanning agent in the solution or dispersion will produce a lighter tan, while the provision of about 1 to about 10%, and preferably about 2 to about 5 percent, of melanin precursor will produce a deeper color.

According to another embodiment of the process of the present invention, an aqueous-alcoholic lotion, containing up to about 50% by volume ethanol or isopropanol, and preferably 5 to 25% by volume ethanol or isopropanol can also be employed.

According to a further embodiment, a cream composition containing a natural tanning assistant, such as 5,6-dihydroxyindole (DHI) and analogs thereof (e.g., 5,6-dihydroxyindole-2carboxylic acid), 5,6-dimethoxyindole, cysteinyl-DOPA and its analogs (e.g., 2-cysteinyl-DOPA; 5-cysteinyl-DOPA) 5,6-methylenedioxyindole or like is applied to the skin prior to exposure to the sun.

In embodiments, the invention concerns cosmetic compositions designed to impart to the skin a coloring which is substantially similar to natural tanning, characterized in that the composition contains, in a cosmetically acceptable base suitable for topical application, at least one compound of formula I:

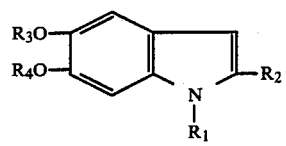
(I)

in which $R_1$ denotes a hydrogen atom or an alkyl group; $R_2$ denotes a hydrogen atom, or a carboxyl group, or a carboxy ester group; and $R_3$ and $R_4$ each denote hydrogen or methyl groups; or $R_3$ and $R_4$ together represent a methylene group which is necessary to complete 5-membered heterocyclic ring; or $R_3$ and $R_4$ are ester groups existing in a ring structure, e.g., a carbonate group.

A preferred group of compounds are of formula II:

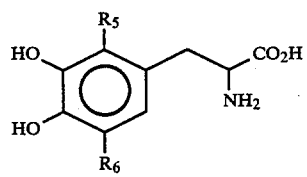
(II)

wherein $R_5$ and $R_6$ are each hydrogen or together are part of a cysteinyl group, i.e., $-S-CH_2CH(NH_2)(CO_2H)$.

The compositions containing tanning assistants, agents or catalysts can be prepared in a manner well known to those skilled in the art. Suitably the concentration of the tanning agent can be between about 0.1 to about 10% and preferably between about 1 to about 5%.

The rate of conversion of the melanin precursors into melanin, either by activation or acceleration, by the actinic energy of sunlight depends on the intensity of the solar radiation and concentration of the ingredients. The development of the melanin requires a time period corresponding to the maximum period for which untanned skin can be safely exposed to sunlight. As the melanin develops, the screening effect against damage increases. During the period of melanin development with the applied composition, a tan develops within the stratum corneum.

This tanning does not interfere with the natural tanning process that takes place in the malphigian layer. When the melanin pigmentation is developed in the stratum corneum, tanning in the malphigian will further augment the filtering of the UVB and UVA light already filtered by the melanin deposit in the stratum corneum.

In addition to providing protection by use of compositions containing a melanin precursor or a melanin precursor like material, it is also possible to employ compositions containing both melanin and one or more melanin precursors or precursor like substances. The melanin in the composition provides an immediate screening effect as well as providing a tanned appearance which esthetically is very desirable for most users.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

The following composition was prepared:
1 g of N-methyl-5,6-diacetoxyindole
1.5 g of isopropyl myristate
8 g of ethyl alcohol
0.5 g of triethanolamine
0.2 of Carbopol 940
water qs to 30 g.

The composition after mixing has the appearance of a thick creamy lotion. When applied to skin and followed by exposure to sunlight, it produced a grey-brown tan.

EXAMPLE 2

The following composition was prepared:
1 g of N-methyl-5,6-dihydroxyindole
5 g of ethyl alcohol
0.1 g of ascorbic acid
0.5 g of hydroxyethyl cellulose
0.2 g of triethanolamine
water qs to 30 g.

The composition after mixing has the appearance of a clear viscous lotion. When applied to skin which has just been washed with a copper salt-containing soap (0.2% of copper), it rapidly yields dark brown coloration similar to extensive darkening produced by sun exposure.

EXAMPLE 3

The following composition was prepared:

1 g of 5,6-methylenedindole
3 g of ethanol
2 g of octyl alcohol
1 g of isopropyl myristate
0.1 g of ascorbic acid
water qs to 30 cc.

The composition after mixing has the consistency of a thin lotion. When applied to skin and followed by exposure to sunlight, it imparted to skin an intense yellow-brown tan.

Additional ingredients can be included in the compositions of the present invention. Accordingly, materials such as polymeric film formers, well known in the prior art and used in cosmetic applications, may be used to protect the applied materials from accidental rub-off or to offer water repellency. Materials of this type include polyvinyl alcohol, cationic polymers such as polyquaternium-8, polyquaternium-4, hydrophobic complexes of cationic polymers with anionic detergents, an example of which may be the complex formed between polyquaternium-6 and ammonium lauryl sulfate, and many others. To enhance both the efficiency of these compositions and their cosmetic appeal, materials well known in the art to achieve these objectives may be added. Examples of these include urea, petrolatum, glycerin, pyrrolidone carboxylic acid, lanolin, ethoxylated long chain alcohols and the like.

Another novel feature of the present invention is that the method can be used to treat the skin condition known as vitiligo. The melanin precursor formulations can be applied to those portions of the skin which are devoid of pigment and then exposed to light. Applications could be repeated until the contrast between the affected area of the skin and the normal area is substantially reduced.

While the present invention has been described by means of the foregoing examples, it is to be understood that the invention is not limited thereto, reference being had to the claims for a definition of the scope of the invention.

We claim:

1. A process for imparting a controlled tan to skin which comprises contacting the skin prior to exposure of same to ultraviolet radiation with a composition substantially free of added enzyme and consisting essentially of about 0.1 to about 10% by weight of at least one tanning agent selected from the group consisting of 5,6-dihydroxy-indoles and a cysteinyl substituted DOPA.

2. The process according to claim 1, wherein the composition is a lotion and the tanning agent is present in an amount of 0.1 to 10 by weight, based on the total weight of the composition.

3. The process according to claim 1, wherein the composition is a creme and the tanning agent is present in an amount of 0.1 to 10% by weight, based on the total weight of the composition.

4. The process according to claim 2, wherein the tanning agent is at least one selected from the group consisting of 3,4-dihydrophenalalanine, a 5,6-dihydroxyindole, and a N-alkyl-5,6-dihydroxyindole.

5. The process according to claim 3, wherein the tanning agent is 5,6-methylenedioxyindole.

6. The process of claim 4, wherein the exposure to ultraviolet radiation is for a period of from about 2 to about 30 minutes.

7. The process of claim 5, wherein the exposure to ultraviolet radiation is for a period of from about 2 to about 30 minutes.

8. The process according to claim 5 wherein the tanning agent is a 5,6-dihydroxyindole.

9. The process according to claim 6 wherein the tanning agent is a N-alkyl-5,6-dihydroxyindole.

10. The process according to claim 6 wherein the tanning agent is 5,6-methylenedioxyindole.

11. A tanning composition consisting essentially of an effective amount of at least one tanning agent selected from the group consisting of 5,6-dihydroxy-indoles and a cysteinyl substituted DOPA, said tanning composition being substantially free of added enzyme, whereby upon application of the composition to skin, color is preferentially generated in the stratum corneum.

12. The composition according to claim 11 wherein the tanning agent is 5,6-methylenedioxyindole.

13. The composition according to claim 11 wherein the tanning agent is 5,6-dihydroxy-N-methylindole.

14. The composition according to claim 11 wherein the tanning agent is 5,6-dihydroxyindole-2-carboxylic acid.

15. The composition according to claim 11 wherein the tanning agent is selected from the group consisting of 2-cysteinyl-DOPA, 5-cysteinyl-DOPA, 2,5-dicysteinyl-DOPA, and mixtures thereof.

16. The composition according to claim 11 wherein the tanning agent is an N-alkyl-5,6-dihydroxyindole.

17. The composition according to claim 12 wherein said tanning agent is present in an amount of about 0.1 to about 10% by weight.

18. The composition according to claim 13 wherein said tanning agent is present in an amount of about 0.1 to about 10% by weight.

19. The composition according to claim 14 wherein said tanning agent is present in an amount of about 0.1 to about 10% by weight.

20. The composition according to claim 15 wherein said tanning agent is present in an amount of about 0.1 to about 10% by weight.

21. The composition according to claim 16 wherein said tanning agent is present in an amount of about 0.1 to about 10% by weight.

22. A cosmetic composition designed to impart to the skin a coloring which is substantially similar to natural tanning, characterized in that it contains, in a cosmetically acceptable base suitable for topical application, an effective amount of at least one compound of formula I or II, wherein formula I is:

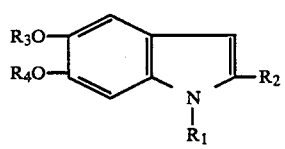

in which $R_1$ denotes a hydrogen atom or an alkyl group; $R_2$ denotes a hydrogen atom, or a carboxyl group; and $R_3$ and $R_4$ each denote hydrogen or methyl groups; or $R_3$ and $R_4$ together represent a methylene group which is necessary to complete a 3-or 5-membered heterocyclic ring; and formula II is:

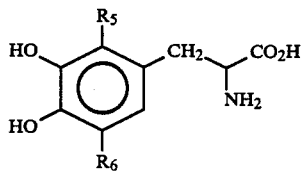

wherein $R_5$ and $R_6$ are each hydrogen or are a part of a cysteinyl group.

23. The compositions of claim 22 containing from about 0.1 to about 10% by weight of the compound of formula I.

24. The composition of claim 22 which also contains at least one ingredient selected from the group consisting of emollients, and perfumes.

25. The composition of claim 22 wherein the cosmetic base contains at least one of ethanol and isopropanol.

26. The composition of claim 22 in the form of a lotion or gel.

27. A process for coloring skin to impart a coloring which is substantially similar to natural tanning comprising the steps of contracting the skin with an effective amount of composition defined in any one of claims 11 to 16, 17 to 21 and 22.

* * * * *